(12) United States Patent
Lee et al.

(10) Patent No.: US 8,158,387 B2
(45) Date of Patent: Apr. 17, 2012

(54) METHOD FOR CELL SURFACE DISPLAY OF TARGET PROTEINS USING FADL OF E. COLI

(75) Inventors: Sang Yup Lee, Daejeon (KR); Seung Hwan Lee, Daejeon (KR); Si Jae Park, Daejeon (KR)

(73) Assignee: Korea Advanced Institute of Science and Technology, Yuseong-Gu, Daejeon (KR)

( * ) Notice: Subject to any disclaimer, the term of this patent is extended or adjusted under 35 U.S.C. 154(b) by 559 days.

(21) Appl. No.: 10/588,782

(22) PCT Filed: Aug. 30, 2004

(86) PCT No.: PCT/KR2004/002181
§ 371 (c)(1),
(2), (4) Date: Aug. 8, 2006

(87) PCT Pub. No.: WO2005/123924
PCT Pub. Date: Dec. 29, 2005

(65) Prior Publication Data
US 2007/0105150 A1 May 10, 2007

(30) Foreign Application Priority Data
Jun. 17, 2004 (KR) .................. 10-2004-0044881

(51) Int. Cl.
*C12P 21/04* (2006.01)
*C12N 1/21* (2006.01)
*C12N 15/00* (2006.01)

(52) U.S. Cl. ............. 435/71.1; 435/320.1; 435/252.3; 435/252.33

(58) Field of Classification Search .......... None
See application file for complete search history.

(56) References Cited

U.S. PATENT DOCUMENTS

| | | | |
|---|---|---|---|
| 5,114,674 A | | 5/1992 | Stanbro et al. |
| 5,508,192 A | * | 4/1996 | Georgiou et al. .......... 435/252.3 |
| 5,807,754 A | | 9/1998 | Zambias et al. |
| 6,071,725 A | * | 6/2000 | Pan et al. ..................... 435/69.7 |
| 6,274,345 B1 | | 8/2001 | Lee et al. |
| 2005/0019857 A1 | | 1/2005 | Lee et al. |

FOREIGN PATENT DOCUMENTS

| | | |
|---|---|---|
| EP | 0 818 467 A2 | 1/1998 |
| KR | 10-2004-0462832 B1 | 12/2004 |
| KR | 10-2004-0462832 B1 | 12/2004 |
| WO | WO-97/42507 A1 | 11/1997 |
| WO | WO-00/54046 A2 | 9/2000 |
| WO | WO-00/61806 A2 | 10/2000 |

OTHER PUBLICATIONS

Park et al., FEMS Micro. Lett., 214, 217-222, 2002.*
DeBoer et al., Proc. Natl. Aca. Sci. USA, 80, 21-25, 1983.*
Lee et al., Trends in Biotechnol., 21, 1, 45-52, 2003.*
Azizan et al., J. Bacteriol. 176, 21, 6653-6662, 1994.*
Agterberg, Marja, et al., Outer-membrane PhoE protein of *Escherichia coli* K-12 as an exposure vector: possibilities and limitations , Gene, Mar. 1990, pp. 37-45, vol. 88, No. 1.
Cadwell, R.C., et al., Randomization of genes by PCR mutagenesis., PCR Methods Appl., Aug. 1992, pp. 28-33, vol. 2, No. 1.
Charbit, Alain, et al., Versatility of a vector for expressing foreign polypeptides at the surface of Gram-negative bacteria , Gene, Oct. 15, 1988, pp. 181-189, vol. 70, No. 1.
Cristalli, Gaetano, et al., The Amino-Terminal Region of the Long-Chain Fatty Acid Transport Protein FadL Contains an Externally Exposed Domain . . . , Arch. Biochem. Biophys., May 15, 2000, pp. 324-333, vol. 377, No. 2.
Francisco, Joseph A., et al. Production and Fluorescence-Activated Cell Sorting of *Escherichia coli* Expressing a Functional Antibody Fragment . . . , Nov. 1993, pp. 10444-10448, vol. 90, No. 22.
Georgiou, George, et al., Practical applications of engineering Gram-negative bacterial cell surfaces, TIBTECH, Jan. 1993, pp. 6-10, vol. 11, No. 1.
Georgiou, George, et al., Display of heterologous proteins on the surface of microorganisms: From the screening of combinatorial libraries to . . . , Nat. Biotechnol., Jan. 1997, pp. 29-34, vol. 15, No. 1.

(Continued)

Primary Examiner — Nancy Vogel
(74) Attorney, Agent, or Firm — Hultquist, PLLC; Kelly K. Reynolds; Steven J. Hultquist

(57) ABSTRACT

The present invention relates to an expression vector which can effectively express target proteins or peptides on the surface of cells using an outer membrane protein (FadL) of *E. coli* as a surface anchoring motif. Also, the present invention relates to microorganisms transformed with the expression vector, and a method for stably expressing large amounts of target proteins on the surface of cells by culturing the transformed microorganisms. Furthermore, the present invention relates to a production method of protein arrays, a production method of antibodies, and a bioconversion method, the methods being characterized by using target proteins which have been expressed on the cell surface by the inventive method. In addition, the present invention relates to a method for improving target proteins by the inventive surface expression method. The present invention allows target proteins with normal functions to be expressed on an outer cell membrane. Thus, the present invention will be useful in recombinant live vaccines, the screening of various peptides or antibodies, whole-cell adsorbents for heavy metal removal or waste water treatment, whole-cell bioconversion, and the like.

8 Claims, 2 Drawing Sheets

OTHER PUBLICATIONS

Kjærgaard, Kristian, et al., Sequestration of Zinc Oxide by Fimbrial Designer Chelators , Appl. Environ. Microbiol., Jan. 2000, pp. 10-14, vol. 66, No. 1.

Kumar, G.B., et al., Bacterial long-chain fatty acid transport. Identification of amino acid residues within the outer membrane protein FadL , J. Biol. Chem., Jul. 25, 1993, pp. 15469-15476, vol. 268, No. 21.

Lång, Hannu, et al., Characterization of adhesive epitopes with the OmpS display system , Eur. J. Biochem., Jan. 2000, p. 163 vol. 267, No. 1.

Lee, Jong-Soo, et al., Surface-displayed viral antigens on Salmonella carrier vaccine, Nature Biotechnology, Jun. 2000, pp. 645-648, vol. 18, No. 6.

Lee, Sang Yup, et al., Microbial cell-surface display, TIBTECH, Jan. 2003, pp. 45-52, vol. 21, No. 1.

Lutz, Stefan, et al., Homology-independent protein engineering , Curr. Opin. Biotechnol., Aug. 1, 2000, pp. 319-324, vol. 11, No. 4.

Martineau, P., et al., A Genetic System to Elicit and Monitor Anti-Peptide Antibodies Without Peptide Synthesis, Bio/Technology, Feb. 1991, pp. 170-172, vol. 9, No. 2.

Ness, Jon E., et al., DNA shuffling of subgenomic sequences of subtilisin, Nat. Biotechnol., Sep. 1999, pp. 893-896, vol. 17, No. 9.

Richins, Richard D., et al., Biodegradation of organophosphorus pesticides by surface-expressed organophosphorus hydrolase , Nat. Biotechnol., Oct. 1997, pp. 984-987, vol. 15, No. 10.

Samuelson, Patrik, et al., Display of proteins on bacteria , J. Biotechnol., Jun. 26, 2002, p. 129-154, vol. 96, No. 2.

Shao, Z., et al., Random-priming in vitro recombination: an effective tool for directed evolution, Nucleic Acids Res., Jan. 1998, pp. 681-683, vol. 26, No. 2.

Sousa,.Carolina, et al., Metalloadsorption by Escherichia coli Cells Displaying Yeast and Mammalian Metallothioneins Anchored to the Outer Membra, J. Bacteriol., May 1998, pp. 2280-2284, vol. 180, No. 9.

Ståhl, Stefan, et al., Bacterial surface display: trends and progress , TIBTECH, May 1997, pp. 185-192, vol. 15, No. 5.

Stemmer, Willem P.C., Rapid evolution of a protein in vitro by DNA shuffling, Nature, Aug. 4, 1994, pp. 389-391, vol. 370, No. 6488.

Zhao, Huimin, et al., Molecular evolution by staggered extension process (StEP) in vitro recombination, Nat. Biotechnol., Mar. 1998, pp. 258-261, vol. 16, No. 3.

Chen, W. et al. , "Cell-Surface Display of Heterologous Proteins: From High-Throughput Screening to Environmental Applications", "Biotechnology Bioengineering", 2002, pp. 496-503, vol. 79, Publisher: Wiley Periodicals.

Lee, S. et al. , "Display of Lipase on the Cell Surface of Escherichia coli Using OprF as an Anchor and its Application to Enantioselectiv", "Biotechnology and Bioengineering", Feb. 20, 2005, pp. 223-230, vol. 90, No. 2.

\* cited by examiner

METHOD FOR CELL SURFACE DISPLAY OF TARGET PROTEINS USING FADL OF *E. COLI*

PRIORITY CLAIM AND CROSS-REFERENCE TO RELATED APPLICATIONS

This application is filed under the provisions of 35 U.S.C. §371 and claims the benefit of priority of International Patent Application No. PCT/KR2004/002181, filed 30 Aug. 2004, which in turn claims priority of Korean Patent Application No. 10-2004-0044881, filed 17 Jun. 2004. The disclosures of all said applications are hereby incorporated herein by reference in their respective entireties.

TECHNICAL FIELD

The present invention relates to a method for stably expressing large amounts of target proteins on the surface of cells using an outer membrane protein (FadL) derived from gram-negative bacteria (*E. coli*). Also, the present invention relates to a production method of protein arrays, a production method of antibodies, and a bioconversion method, the methods being characterized by using target proteins which have been expressed on the cell surface by said method. In addition, the present invention relates to a method for improving target proteins using the inventive surface expression method.

BACKGROUND ART

Cell surface display refers to a technology of expressing proteins or peptides in a form fused with a suitable surface anchoring motif on the surface of cells, such as gram negative and positive bacteria, molds, yeasts and animal cells (Lee, S. Y. et al., *Trend. Biotechnol.*, 21:4552, 2003). In 1980s, the surface-expression system was first developed by expressing peptides or small proteins fused with pIII of a filamentous phage with a relatively simple surface. Although the cell surface display using the phage was used in the screening of antibodies, epitopes, high-affinity ligands and the like, the size of proteins which can be expressed on the phage surface is relatively limited. Thus, as an alternative substitute therefor, a cell surface expression method for stably expressing foreign proteins on the surface of microorganisms using a surface protein of microorganisms, such as bacteria or yeasts, as a surface anchoring motif, has been developed.

In order to express a foreign protein on the surface of cells using the outer membrane protein of a certain organism, a suitable surface protein and the foreign protein should be linked with each other at a gene level to biosynthesize a fusion protein, which should be stably passed through a cell inner membrane and attached, and then maintained on the cell surface. For this purpose, a protein having the following properties is preferably selected for use as a matrix for surface expression. Namely, (1) it has a secretion signal capable of passing through the cell inner membrane, at the N-terminal end; (2) it must have a targeting signal which can be stably attached on the surface of a cell outer membrane; (3) it can be expressed on the cell surface in large amounts within range of having no adverse effect on the growth of cells, such that the protein can show high activity; and (4) it is stably expressed regardless of its size such that it should be able to be used in various reactions (Georgiou et al., *Trend. Biotechnol.*, 11:6, 1993). Such a matrix for surface expression needs to be genetically engineered such that it is inserted into the N-terminal end, C-terminal end or central portion of the outer membrane protein on the surface of the host cells (Lee et al., *Trend. Biotechnol.*, 21:45-52, 2003).

In order to successfully express target peptide or protein on the surface of bacteria, such as *E. coli* with a complex membrane structure, it is first required to select a surface anchoring motif by which foreign proteins to be expressed on the cell surface can be stably and efficiently transported to the cell surface. Surface anchoring motifs which have been used in *E. coli* till now include outer membrane proteins, lipoproteins, autotranspoters, the subunits of surface appendages, and S-layer proteins. Among them, the outer membrane proteins have several advantages such as efficient secretory signal, unique membrane spanning structures providing fusion sites, and strong anchoring structures. Owing to such advantages, the outer membrane proteins have been frequently used as a surface anchoring motif.

Outer membrane proteins such as OmpA, OmpS, LamB, OprF, PhoE and the like have widely been used for the expression of peptides, antibodies, domains, receptors, which have a relatively small molecular weight (Agterberg, M. et al., *Gene*, 88:37, 1990; Lang, H. et al., *Eur. J. Bacteriol.*, 267:163, 2000). Since the C-terminal and N-terminal ends of inserted foreign proteins must be placed close to each other in three dimensions, these cell surface display system show low stability for the large protein. In fact, if LamB or PhoE is inserted with a foreign protein comprised of 50-60 or more amino acids, it will encounter limitations in its structure, which make it impossible to form a stable membrane protein. Also, *E. coli* porin (outer membrane protein) was used only in epitopes or metal binding motifs other than proteins comprised of at most 150 amino acids (Stahl, S. et al., *Trends Biotechnol.*, 15:185, 1997; Kjaergaad, K. et al., *Appl. Environ. Microbiol.*, 66:10, 2000).

Cell surface display using a bacterial secretion system is used in a very wide range of applications. Also, it can be used in various applications depending on proteins or peptides which are expressed on the cell surface. The expression of a certain protein on the cell surface allows simple screening of peptides, antibodies or receptors (Francisco, J. A. R. et al., *PNAS*, 91:10444, 1993), and the expression of antigen epitopes on the cell surface allows the production of live vaccines which can show a powerful immune response. Also, a certain enzyme required in fine chemicals, agricultural chemicals or medicines, which have been expressed on the cell surface, may be used as a whole-cell biocatalyst, or proteins capable of degrading contaminants or adsorbing metal ions, which have been expressed on the cell surface, may be used in bioremediation (Charbit, A. et al., *Gene*, 70:181, 1988; Sousa, C. et al., *J. Bacteriol.*, 180:2280, 1998; Richins, R. et al., *Nat. Biotechnol.*, 15: 984, 1997).

Various kinds of surface anchoring motifs have been reported till now. However, targets which can be expressed on the cell surface by one surface anchoring motif are limited, so that the development of surface anchoring motifs which is different from each other, is needed to express various proteins on the cell surface.

FadL from *E. coli* which is a protein associated with the fatty acid metabolism of *E. coli* is involved in fatty acid transport. Regarding the membrane topology of the FadL protein, the N-terminal and C-terminal ends of the protein are found in the peripheral cytoplasm, 10 loops are out of the outer cell membrane, and 9 loops are out towards the peripheral cytoplasm (Cristalli et al., *Arch. Biocheem. Biophys.*, 377: 324, 2000).

Since FadL is a protein of *E. coli* itself, it can easily express foreign proteins in a form fused with the foreign protein using *E. coli* as a host cell. Also, this protein has 10 external, loops providing various points which can be fused, thus, it is expected that the FadL protein can increase the possibility of cell surface expression of foreign proteins. Furthermore, the FadL protein has a stability that has been pointed out as a shortcoming of enzymes expressed on the cell surface in several surface expression systems. In other words, this protein has an advantage in that it allows the enzymes expressed on the cell surface to maintain their activity for a long time period under various conditions (high temperature, high pH, organic solvent, etc.).

Accordingly, the present inventors have truncated a gene following the ninth loop expected to have the highest expression possibility of 10 loops which are out of the outer cell membrane in the outer membrane protein, fused a foreign protein (lipase) to the truncated loop position of E. coli, and expressed the lipase on the surface of cells. As a result, the present inventors confirmed that the lipase expressed on the cell surface is useful in bioconversion reactions, thus perfecting the present invention.

DISCLOSURE OF INVENTION

It is an object of the present invention to provide a surface expression vector of a target protein containing not only a fadL gene encoding an E. coli outer membrane protein (FadL) but also a gene encoding a target protein.

Another object of the present invention is to provide microorganisms transformed with said surface expression vector, and a method for the cell surface expression of a target protein, which is characterized by culturing the transformed microorganisms.

Still another object of the present invention is to provide a method for the production of protein arrays, a method for the production of antibodies in vertebrate animals, and a bioconversion method, the methods being characterized by using cells which are produced by said expression method and have a target protein expressed on the surface thereof.

To achieve the above objects, in one aspect, the present invention provides a vector for expressing a target protein on the surface of cells, the vector comprising a fadL gene encoding an E. coli outer membrane protein (FadL), an antibiotic-resistant gene, a promoter, a gene encoding a target protein, and a gene recombinant which is constructed to be expressed on the surface of the cell in a form fused with the FadL protein if the target protein-encoding gene is expressed in a host cell.

In a preferred embodiment of the inventive surface expression vector for the target proteins, a linker is inserted into the middle portion of the fadL gene, and a target protein-encoding gene is inserted into the linker. Alternatively, the C-terminal end of the fadL is truncated, and the target protein-encoding gene is inserted into the position of the truncated C-terminal end. Alternatively, a base sequence following the ninth loop of the fadL gene is truncated, and the target protein-encoding gene is inserted into the position of the truncated base sequence.

In a preferred embodiment of the inventive surface expression vector, the target protein is a protein with a portion of amino acid sequence eliminated, or a protein mutated position-specifically, to facilitate the expression of the target protein on the surface. The promoter is preferably a Tac promoter or a gntT104 promoter, and it is obvious to a person skilled in the art that the target protein can be expressed by a suitable promoter whose expression can be induced in a host cell, by a promoter of the target protein gene, or by other suitable promoters which can be expressed in host bacteria.

In another aspect, the present invention provides microorganisms transformed with the above-described surface expression vector. In the present invention, microorganisms used for the transformation are modified, such that an extracellular or intracellular protease that degrades the target protein, cannot be produced, facilitate the cell surface expression of the target protein. Also, the microorganisms are preferably bacteria.

In still another aspect, the present invention provides a method for the cell surface expression of a target protein, the method comprising the steps of culturing said transformed microorganisms to express a target protein on the cell surface of the microorganisms, and collecting the cells having the target protein expressed on the surface thereof.

In yet another aspect, the present invention provides a bioconversion method characterized by using the cells which are produced by said method and have a target protein with enzymatic activity expressed on the surface thereof. As a catalyst substance for bioconversion reaction in this method, any biosubstance which can catalyze chemical reactions can be used after fusion expression with a FadL protein. Examples of the catalyst substance include enzymes and catalytic antibodies.

In a further aspect, the present invention provides a method for producing protein arrays, characterized by immobilizing the cells, which are produced by said method and have a target protein expressed on the surface thereof, on the surface of a substrate.

A protein array, arrays various proteins such as a DNA array or a DNA chip, particularly antibodies, on a solid surface, so that it provides a means capable of analyzing the expression and expression level of the desired target protein in certain cells. To prepare a protein array, proteins to be arrayed, should be secured and immobilized on a solid surface. In an analysis process using the protein array, in order to bind immobilized proteins and to wash unbound proteins, various treatments, such as heating and changes in salt concentration and pH, are conducted, thus, the immobilization of a stabilized protein capable of resisting this severe environment is required. However, in cloning several thousand to tens of thousands of genes into an expression vector, and expressing and separating them and then immobilizing them on a solid surface, many operations should be conducted in a repeated manner. Thus, such operations need to be conducted in a more simple and rapid manner.

The method for producing the protein array according to the present invention provides a means allowing such operations to be conducted most easily. For the production of the protein array according to the present invention, the method which is conventionally used in the art can be applied (WO 00/61806; WO 00/54046; U.S. Pat. No. 5,807,754; EP 0818467; WO 97/42507; U.S. Pat. No. 5,114,674; and WO 96/35953). The protein array produced by the inventive method can be used in a diagnostic kit, gene expression analysis, the analysis of protein-protein, protein-ligand or antigen-antibody interactions, metabolic process analysis, the screening of a new enzyme or improved enzyme, combinatorial biochemical synthesis, and biosensors.

Examples of solid substrates which can be used in the inventive production method of the protein arrays include glass (e.g., glass having functional groups exposed to the outside), Si, Ge, GaAs, GaP, SiO, SiN4, modified silicon nitrocellulose, polyvinylidene fluoride, polystyrene, polytetrafluoroethylene, polycarbonate, nylon, fiber, and a combination thereof. A linker molecule for protein immobilization may also be attached to the substrate, in which non-spotted portions of the substrate is preferably blocked. Meanwhile, the amount of the cells expressed according to the present invention, which are applied to each of the spot (or address), is determined depending on the form of the arrays. An interaction between a sample and the inventive surface-expressed protein immobilized on the solid substrate may be either detected using the inherent characteristics of the protein (e.g., immune reactivity), or detected by a change in the signal of a suitable marker substance (e.g., fluorescent substance, luminescent substance, radioactive substance or epitope) linked to the protein. The analysis of results obtained by the inventive protein arrays can be performed by an automated system which is known as "scanner" or "reader" in the art.

In still another aspect, the present invention provides a method for preparing antibodies in vertebrate animals, the method comprising the steps of: administering the cells which are produced by said method and have antigens expressed on the surface thereof, to the vertebrate animals except for human beings, thereby inducing an immune response in the vertebrate animals; and collecting antibodies produced by the immune response.

The surface expression technology as described above expresses an antigen or a part thereof on the cell surface to produce an antibody so that it provides a transfer means of recombinant live vaccine using the same. In the vaccines developed till now, attenuated pathogenic bacteria or viruses were mainly used, and in the case of the bacteria, an antigen was secreted and expressed inside a cell, on a cell membrane, or outside a cell, and transferred to a host cell. Since the surface-expressed live vaccine shows a very strong immune response and can express an antigen continuously while growing in a host cell, it is noticed as a new vaccine transfer means. Particularly, when a pathogen-derived aritigenic epitope is expressed on the surface of non-pathogenic *E. coli* or *Salmonella* sp. and orally administered alive, it is known to show far more lasting and strong immunity, so that it can be used as a method for inducing antigen-antibody production (Georgiou et al., *Nature Biotechnol.*, 15:29, 1997; and Lee et al., *Nature Biotechnol.*, 18:645, 2000).

Martineau et al., reported a very simple method of producing an antipeptide antibody using the expression technology on the *E. coli* surface (Martineau et al., *Bio/Technol.*, 9:170, 1991). In this surface expression technology, the desired peptide is expressed on the surface protrusions of MalE and LamB which is a cell outer membrane, and then, the whole cell or ground cell is administered to an animal to induce the production of an antipeptide antibody. According to this method, the antibody can be produced without chemically synthesizing peptide or attaching it to a transfer protein.

The cells having antigens expressed on the surface thereof, which are used in the inventive production method of antibodies, are preferably safe cells for a subject to be administered, and preferably contain an adjuvant, such as incomplete or complete Freud's adjuvant. Meanwhile, the cells are preferably administered by injection, and more preferably an intravenous, celiac, subcutaneous or intramuscular administration. In order to obtain a sufficient amount of the antibodies, the booster administration of the cells is preferably performed at a suitable time after the first administration of the cells.

In yet another aspect, the present invention provides a method for producing a chiral compound, which comprises optically resolving racemic compounds into chiral compounds by enantioselective target protein, the method being characterized by using the lipase expressed on the surface of the cells produced by said method.

In further another aspect, the present invention provides a method for improving a target protein, the method comprising the steps of: (a) constructing a mutant library of a gene encoding a target protein; (b) constructing a gene recombinant which contains the gene mutant library of the target protein and a fadL gene to express the mutant of the target protein in a form fused with a FadL protein; (c) transforming a host cell with either the gene recombinant or a vector containing the gene recombinant, the host cell being selected from the group consisting of gram negative bacteria, gram positive bacteria, actinomyces, yeasts and molds; (d) culturing the transformed host cells to express the gene mutant library on the cell surface; and (e) screening the cells on which a target protein with improved characteristics have been expressed.

In the method for the improvement of a target protein according to the present invention, the gene library can be obtained by modifying the gene of a wild-type target protein using DNA shuffling (Stemmer, *Nature*, 370:389, 1994), StEP (Zhao, H. et al., *Nat. Biotechnol.*, 16: 258, 1998), RPR (Shao, Z. et al., *Nucleic Acids Res.*, 26:681, 1998), molecular breeding (Ness, J. E. et al., *Nat. Biotechnol.*, 17:893, 1999), ITCHY (Lutz, S. et al., *Cur. Opi. Biotechnol.*, 11:319,2000), error-prone PCR (Cadwell, R. C. et al., *PCR Method App.*, 2:28, 1992), and point mutation (Sambrook et al., *Molecular Cloning: A Laboratory Manual*, Cold Spring Harbor, N.Y., 1989), but is not limited thereto.

In the target protein improvement method of the present invention, the screening step is characterized by using the activity of a target protein, a protein recognizing substance labeled to a target protein, a labeled ligand binding to a target protein, or an antibody binding specifically to a target protein. Also, the screening step can be conducted by using a flow cytometer (Georgiou, G., *Adv. Protein Chem.*, 55:293, 2000), and in the case of using the protein activity, the screening can be achieved by either measuring the growth of a host in which a protein is expressed, or measuring the color development reaction catalyzed by the protein.

In the case of using the inventive protein improvement method having the above characteristics, an enzyme catalyzing chemical reaction that does not occur biologically (e.g., Diels-Alder condensation), an enzyme with unnatural stereoselectivity or regioselectivity, an enzyme capable of catalyzing reaction in an organic solvent or a higher solution than organic solvent-aqueous solution, and an enzyme catalyzing reaction in extreme conditions such as high temperature and high pressure, etc., which cannot be easily obtained by the prior method, can be rapidly obtained from wild-type enzymes.

The inventive method can be applied to all proteins. For example, the inventive method can be used for the surface expression and improvement of a target protein selected from the group consisting of hormones, hormone analogues, enzymes, enzyme inhibitors, signaling proteins or parts thereof, antibodies or parts thereof, single chain antibodies, binding proteins, binding domains, peptides, antigens, adhesion proteins, structural proteins, regulatory proteins, toxin proteins, cytokines, transcriptional regulators, blood coagulation factors, and plant defense-inducing proteins.

DETAILED DESCRIPTION OF THE INVENTION

The present invention will hereinafter be described in further detail by examples. It will however be obvious to a person skilled in the art that these examples are given for illustrative purpose only, and the scope of the present invention is not limited to or by these examples.

Although a bioconversion reaction using lipase is particularly illustrated in the following examples, it will be obvious to a person skilled in the art from the disclosures herein that the inventive method may utilize any enzyme expressed on a cell surface, such as beta-galactosidase, protease, cellulase, glycosyltransferase, oxidoreductases, and aldolase. Also, the inventive method may be applied to the case where the bioconversion reaction is monostep or multistep and be applied even to the case where the bioconversion reaction occurs in an aqueous or non-aqueous phase. Cells having enzymes expressed on the surface thereof may be used in an immobilized or non-immobilized state, and the bioconversion may be used in combination with other microorganisms or enzymes.

EXAMPLE 1

Construction of Recombinant Vector (pTrcFadL)

In order to express an outer membrane protein on Trc promoter, a pTrcFadL which is a recombinant plasmid containing a trc promoter was prepared.

In order to obtain $E.$ $coli$ outer membrane protein (FadL) gene from which the C-terminal end has been removed, 30-cycle PCR on the chromosomal DNA of $E.$ $coli$ W3110 (ATCC 39936) as a template was performed with primers of SEQ ID NO: 1 and SEQ ID NO: 2. In the PCR reaction, each PCR cycle consisted of first denaturation for 5 minutes at 95° C., second denaturation for 30 seconds at 95° C., annealing for 1 minute at 50° C., and extension for 1 minute and 30 seconds at 72° C.

```
SEQ ID NO: 1:  5-ggaattcatggtcatgagccagaaaacc

SEQ ID NO: 2:  5-gctctagaacgattctgtgcaggaac
```

Figure 1:
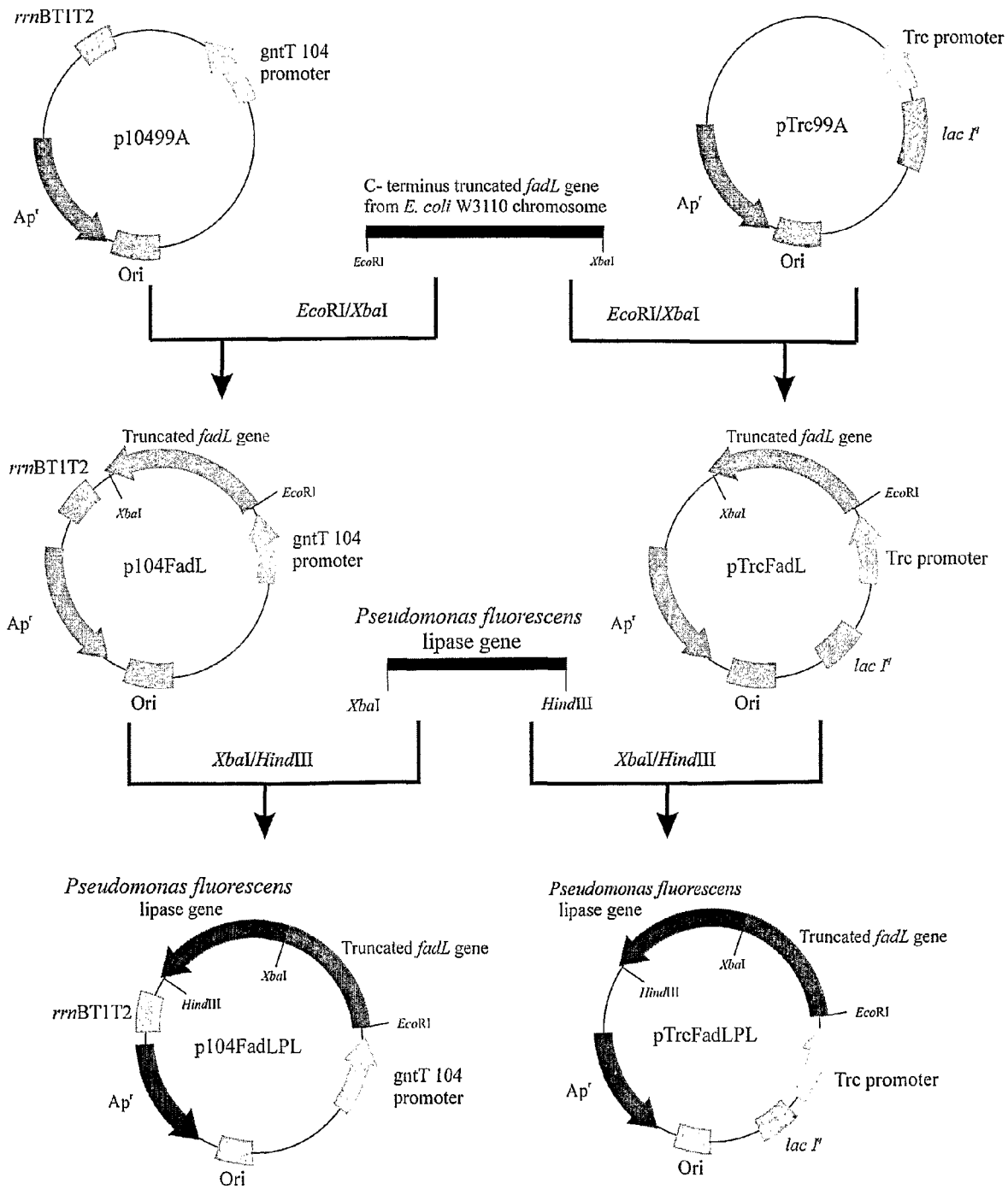
FIG. 1 shows recombinant plasmids pTrcFadLPL and p104FadLPL according to the present invention.

From a fragment obtained by the PCR reaction, a DNA fragment with the size of about 1100 bp was separated by agarose gel electrophoresis, and cut with restriction enzymes EcoRI and XbaI. The cut fragment was linked with a DNA fragment which has been obtained by cutting trc promoter-containing plasmid pTrc99A (Pharmacia Biotech., Uppsala, Sweden) with restriction enzymes EcoRI and XbaI, thus obtaining recombinant plasmid. The resulting recombinant plasmid was transformed into $E.$ $coli$ XL10-Gold by electroporation, and then the transformed strains were selected on an LB plate medium containing 50 μg/L of ampicillin, thereby obtaining a pTrcFadL recombinant plasmid (see FIG. 1).

EXAMPLE 2

Preparation of Recombinant Vector (p104FadL)

In order to express an outer membrane protein on a constitutive promoter, recombinant plasmid p104FadL containing a gntT104 promoter was prepared. Namely, a DNA fragment obtained by cutting gntT104 promoter-containing plasmid p10499a (Park, S. J. et al., $FEMS$ $Microbiol.$ $Lett.$, 214:217, 2002) with restriction enzymes EcoRI and XbaI was linked to the $E.$ $coli$ outer membrane protein (FadL) gene from which the C-terminal end has been removed, obtained in Example 1, thus constructing a recombinant plasmid. The obtained recombinant plasmid was transformed into $E.$ $coli$ XL10-Gold (Stratagene Co.) by electroporation. The transformed strains were selected on an LB plate medium containing 50 μg/L of ampicillin, thus obtaining a p104FadL recombinant plasmid (see FIG. 1).

EXAMPLE 3

Preparation of Recombinant Expression Vector (pTrcFadLPL and p104FadLPL)

In order to prepare a recombinant plasmid which expresses lipase on the surface of cells, the lipase gene of $Pseudomonias$ $fluorescens$ was first constructed in the following manner. Namely, 30-cycle PCR on the chromosomal DNA of $Pseudomonas$ $fluorescens$ as a template was performed with primers of SEQ ID NO: 3 and SEQ ID NO: 4. In the PCR reaction, each PCR cycle consisted of first denaturation for 5 minutes at 95° C., second denaturation for 45 seconds at 95° C., annealing for 45 seconds at 60° C., and extension for 1 minute and 30 seconds at 72° C.

```
SEQ ID NO: 3:  5-gctctagaatgggtgtatttgactacaagaac

SEQ ID NO: 4:  5-cccaagctttcaactgatcagcacacc
```

From the DNA fragment obtained by the PCR reaction, a lipase gene, a DNA fragment with the size of about 1.4 kbp, was obtained by agarose gel electrophoresis. The lipase gene was cut with xbaI and HindIII, and inserted into each of pTrcFadL and p104FadL, thus preparing recombinant expression vectors pTrcFadLPL and p104FadLPL, respectively. The obtained vectors we're transformed into $E.$ $coli$ XL10-Gold. The transformed strains were screened in an LB plate medium containing 50 μg/L of ampicillin, and the screened strain was cultured in an LB liquid medium, and then stored in a freezer at −80° C. (see FIG. 1).

EXAMPLE 4

Cell Surface Expression of Lipase

Figure 2:
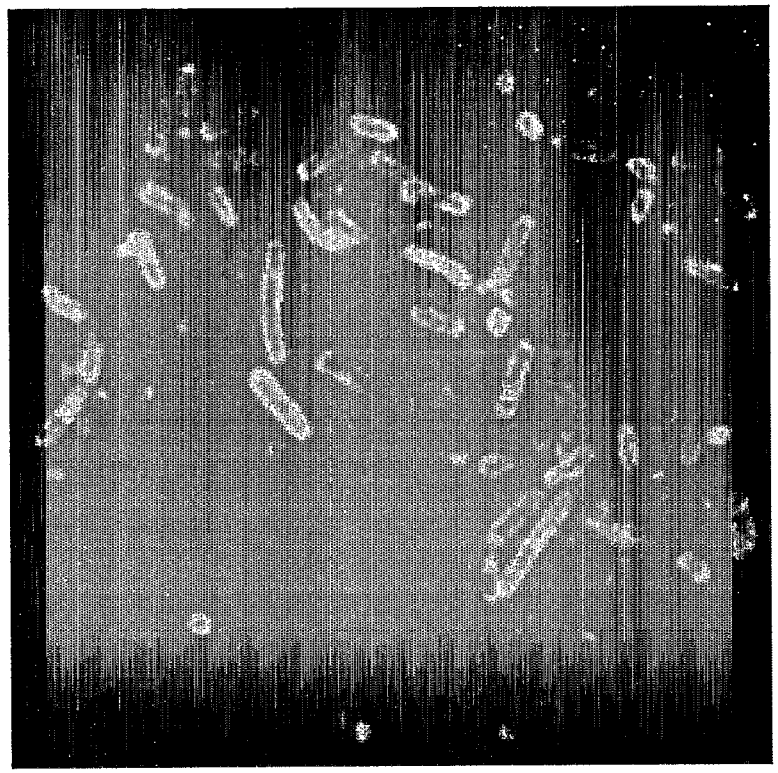
FIG. 2 shows a confocal microscopy photograph for lipase expressed on the surface of cells.

The transformed strain XL10-Gold (pTrcFadLPL) prepared in Example 3 was inoculated into 10 ml of an LB liquid medium containing 50 μg/L of ampicillin and cultured at 37° C. When the absorbance at a 600 nm wavelength by a spectrophotometer reached 0.5, 0.1 mM IPTG was added to the medium so as to induce gene expression. 5 hours after the gene expression induction, the culture broth was centrifuged at 4° C. and 6000 rpm for 5 minutes to collect cells, and the collected cells were washed with phosphate buffered saline solution (PBS, pH 7.2), and then re-suspended in a PBS solution containing 3 wt % bovine serum albumin (BSA). Rat anti-lipase serum, a primary antibody, was added to the 3 wt % BSA-containing PBS solution at a ratio of 1:1000, and then cultured at 4° C. for 4 hours. The culture medium was washed five times with PBS solution, after which Texas Red-conjugated secondary antibody (goat anti-rat IgG) was added to the resulting culture medium at a ratio of 1:3000 and then cultured at 4° C. for 12. hours. In order to remove unreacted secondary antibody, the culture medium was washed five times with PBS solution, and observed under a confocal microscope (Carl Zeiss, Jena, Germany). The observation results showed that lipase was expressed on the cell surface (see FIG. 2).

EXAMPLE 5

Activity of Lipase Expressed on Cell Surface

Figure 3:
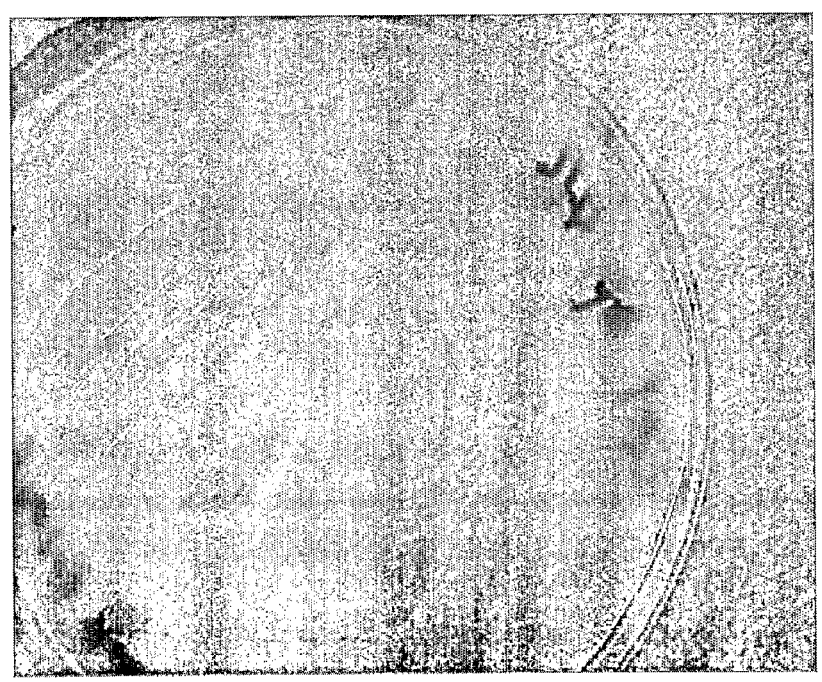
FIG. 3 shows a plate photograph for proving the activity of lipase expressed on the surface of cells.

The transformed strain XL10-Gold (p104FadLPL) prepared in Example 3 was cultured in an LB plate medium containing 50 µg/L of ampicillin and 1% (v/v) of tributyrin. After 72 hours, halo was produced in the medium due to the activity of lipase (see FIG. 3).

EXAMPLE 6

Optical Resolution of Racemic Mandelic Acid Methyl Ester Using Lipase Expressed on Cell Surface The transformed strain XL10-Gold (pTrcFadLPL) prepared in Example 3 was inoculated again in 250 mL Erlenmeyer flask including 100 mL of LB liquid medium containing 50 µg/L of ampicillin, and then cultured at 37° C. Gene expression was induced by adding 0.1 mM of IPTG, when absorbance was 0.5 at 600 nm wavelength by spectrophotometer. 5 hours after inducing the expression, culture broth was centrifuged at 4° C., 600 rpm for 5 minutes to collect cells, and then, the collected cells were washed with 50 mM Tris-HCl solution (pH 8.0), followed by resuspending in 3 mL of buffer. Said re-suspension was put into a 10 mL flask, to which 30 mg of racemic mandelic acid methyl ester was added and allowed to react for 48 hours with stirring. Then, the suspension was centrifuged at 4° C. and 6000 rpm for 5 minutes to remove cells. The supernatant was collected and adjusted to a pH of 3.0. After extraction of the supernatant with 10 mL of ethyl acetate and hexane, the extract was analyzed by liquid chromatography. The analysis results showed that (S)-mandelic acid and (R)-mandelic acid methyl ester were obtained.
HPLC Analysis Conditions:
column: Chiralcel OD-H;
flow rate: 0.5 mL/min;
solvent:hexane:iso-propanol:tri-fluoroacetic acid=90:10:0.1 (volume ratio);
detect: UV 254 nm.

EXAMPLE 7

Optical Resolution of Racemic β-lactam, racemic cis-3-acetoxy-4-phenylazetidin-2-one Using Lipase Expressed on Cell Surface Cells were collected in the same manner as in Example 6, and suspended in 3 mL of 0.1M sodium phosphate buffer (pH 6.8). 20 mg of recemic β-lactam and racemic cis-3-acetoxy-4-phenylazetidin-2-one were added to the suspension and allowed to react for 24 hours with stirring. At this time, the reaction sample was applied to thin film chromatography (TLC) [chloroform:ethyl acetate:hexane=3:2:3(volume ratio)] so as to check the progression of the reaction.

After completion of the reaction, the resulting material was centrifuged at 6000 rpm for 7 minutes to remove cells. The supernatant was collected and extracted five times with 10 mL of ethyl acetate. The solvent was removed with a vacuum rotary distillation/concentration device, and the remaining material was applied to silica gel column chromatography. As a result, chiral β-lactam, 8 mg of (−)-cis-3-hydroxy-4-phenylazetidin-2-one (40% yield) and 6 mg of (−)-cis-3-acetoxy-4-phenylazetidin-2-one (30% yield) were obtained.

(−)-cis-3-hydroxy-4-phenylazetidin-2-one

[α]D-130o(c 0.5, CH3OH);
1H NMR (CDCl3 & DMSO-d6) δ 3.60(s, 1 H, OH), 4.95 (d, J=4.7 Hz, 1H, C3 H), 5.88(d, J=4.7 Hz, 1H, C4H), 6.22(s, 1H, NH), 7.27-7.40(m, 5H, ArH);
13C NMR(CDCl3 & DMSO-d6) δ 58.6, 79.1, 127.6, 128.1, 137.1, 170.5;
CIMS, m/z 163(M+), 91(base).

(−)-cis-3-acetoxy-4-phenylazetidin-2-one

[α]D-30o (c 1, CHCl3); IR (KBr) 3200, 1750, 1720 cm-1
1H NMR(CDCl3) δ 1.68(s, 3H, CH3CO), 5.05(d, J=4.5 Hz, 1H, C3H), 5.88(dd, J=2.6 & 4.5 Hz, 1H, C4H), 6.25(s, 1H, NH), 7.29-7.39(m, 5H, Ar);
13C NMR(CDCl3) δ 19.7, 57.9, 78.3, 127.5, 127.7, 128.2, 128.5, 134.7, 165.6((β-lactam CO), 169.0(acetoxy CO);
CIMS, m/z 205(M+), 106(base).

EXAMPLE 8 pH Stability of Lipase Expressed on Cell Surface

Cells were collected in the same manner as in Example 6, and suspended in 3 mL of Tris-HCl buffer (pH 10.0). 100 µl of the suspension was taken every hour and measured for activity. The results showed that more than 90% of the initial activity was maintained even after 48 hours. The activity measurement was conducted in the following manner. The taken sample was centrifuged at 4° C. and 6000 rpm for 5 minutes to collect cells, and the collected cells were suspended in a solution prepared by mixing a solution of 10 mM p-nitrophenyl decanoate in acetonitrile, ethanol and Tris-HCl buffer (pH 8.0), at a volume ratio of 1:4:95, and the suspension was allowed to react at 37° C. for 10 minutes. After the reaction was terminated by the addition of 2 µl of 0.5M EDTA solution, the activity was calculated by measuring the absorbance at 405nm.

EXAMPLE 9

Temperature Stability of Lipase Expressed on Cell Surface

Cells were collected in the same manner as in Example 6, and suspended in 3mL of Tris-HCl (pH 8.0). The suspension was left as it was at 50° C., and measured for the activity. The results showed that more than 90% of the activity was maintained even after 120 hours.

EXAMPLE 10

Organic Solvent Stability of Lipase Expressed on Cell Surface

Cells were collected in the same manner as in Example 6, and suspended in 3 mL of hexane. The suspension was left as it was at 37° C. and measured for the activity. The results showed that the activity was maintained for 48 hours.

As confirmed in Examples 6 to 10, lipase which has been normally expressed on the cell surface by the inventive method may be used in the preparation of chiral compounds. Also, it is easy to recover the lipase and its stability is excellent, so that it can make the preparation process of chiral compounds simple and can increase the productivity in the preparation process of chiral compounds.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

INDUSTRIAL APPLICABILITY

As described above, the present invention provides the expression vector which can effectively express target proteins or peptides on the surface of cells using an outer membrane protein (FadL) of *E. coli* as a surface anchoring motif, microorganisms transformed with the expression vector, and a method for stably expressing large amounts of target proteins on the surface of cells by culturing the transformed microorganisms.

The present invention allows target proteins with normal functions to be expressed on the outer membrane of cells. Thus, the present invention will be useful in recombinant live vaccines, the screening of various peptides or antibodies, whole-cell adsorbents for heavy metal removal or waste water treatment, whole-cell bioconversion, and the like depending on target proteins inserted.

What is claimed is:

1. A vector for expressing a target protein on the surface of cells, the vector comprising a fadL gene encoding an *E. coli* outer membrane protein (FadL) in which (nucleotides 1156-1347 of the fadL gene have been removed, an antibiotic-resistant gene, a promoter, and a gene encoding a target protein, in which the recombinant gene is constructed such that if the target protein-encoding gene is expressed in a host cell, it is expressed on the surface of the cell in a form fused with the FadL protein, wherein the target protein-encoding gene is positioned after the fadL gene fragment.

2. The vector for expressing a target protein on the surface of cells according to claim 1, wherein the promoter is a Tac promoter or a gntT104 promoter.

3. A microorganism transformed with the surface expression vector of claim 1.

4. The transformed microorganism according to claim 3, wherein the microorganism is bacterium.

5. The transformed microorganism according to claim 4, wherein the bacterium is *E. coli*.

6. A method for the cell surface expression of a target protein, the method comprising the steps of: culturing the transformed microorganism of claim 3, to express a target protein on the cell surface of the microorganisms, and collecting the cells having the target protein expressed on the surface thereof.

7. The method for the cell surface expression of a target protein according to claim 6, wherein the target protein is selected from the group of hormones, hormone analogs, enzymes, enzyme inhibitors, signaling proteins or parts thereof, antibodies or parts thereof, single chain antibodies, binding proteins, binding domains, peptides, antigens, adhesion proteins, structural proteins, toxin proteins, cytokines, transcriptional regulators, blood coagulation factors, and plant defense-inducing proteins.

8. The method for the cell surface expression of a target protein according to claim 7, wherein the enzyme is lipase.

\* \* \* \* \*

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial
<220> FEATURE:
<223> OTHER INFORMATION: PCR primer

<400> SEQUENCE: 1
ggaattcatg gtcatgagcc agaaaacc                                       28

<210> SEQ ID NO 2
<211> LENGTH: 26
<212> TYPE: DNA
<213> ORGANISM: Artificial
<220> FEATURE:
<223> OTHER INFORMATION: PCR primer

<400> SEQUENCE: 2
gctctagaac gattctgtgc aggaac                                         26

<210> SEQ ID NO 3
<211> LENGTH: 32
<212> TYPE: DNA
<213> ORGANISM: Artificial
<220> FEATURE:
<223> OTHER INFORMATION: PCR primer

<400> SEQUENCE: 3
gctctagaat gggtgtattt gactacaaga ac                                  32

<210> SEQ ID NO 4
<211> LENGTH: 27
<212> TYPE: DNA
<213> ORGANISM: Artificial
<220> FEATURE:
<223> OTHER INFORMATION: PCR primer

<400> SEQUENCE: 4
cccaagcttt caactgatca gcacacc                                        27
```